United States Patent
Jeong et al.

(10) Patent No.: US 12,156,784 B2
(45) Date of Patent: Dec. 3, 2024

(54) METHOD FOR OBTAINING SUBGINGIVAL MARGINAL SHAPE FOR PROSTHESIS DESIGN NON-INVASIVELY

(71) Applicants: Huvitz Co., Ltd., Anyang-si (KR); Ossvis Co., Ltd., Anyang-si (KR)

(72) Inventors: Hyo Sang Jeong, Daegu (KR); Su Min Han, Seoul (KR); Weon Joon Lee, Anyang-si (KR)

(73) Assignees: HUVITZ CO., LTD., Anyang (KR); OSSVIS CO., LTD., Anyang (KR)

( * ) Notice: Subject to any disclaimer, the term of this patent is extended or adjusted under 35 U.S.C. 154(b) by 374 days.

(21) Appl. No.: 17/676,113

(22) Filed: Feb. 18, 2022

(65) Prior Publication Data

US 2022/0265400 A1 Aug. 25, 2022

(30) Foreign Application Priority Data

Feb. 19, 2021 (KR) ........................ 10-2021-0022390

(51) Int. Cl.
*A61C 9/00* (2006.01)
*A61B 5/00* (2006.01)
*G06T 19/20* (2011.01)

(52) U.S. Cl.
CPC .......... *A61C 9/0053* (2013.01); *A61B 5/0066* (2013.01); *A61B 5/0088* (2013.01);
(Continued)

(58) Field of Classification Search
CPC ....... A61C 9/0053; A61C 5/77; A61C 9/0073; A61C 13/0004; A61C 9/0046; A61C 5/70; A61B 5/0066; A61B 5/0088; A61B 5/0062; A61B 2018/20353; A61B 2034/102; G06T 19/20; G06T 2207/30036; G06T 2219/2004; G06T 2210/41; G06T 2219/20;
(Continued)

(56) References Cited

U.S. PATENT DOCUMENTS

2012/0322025 A1 12/2012 Ozawa et al.
2015/0348320 A1* 12/2015 Pesach ................ A61C 19/043
  382/128

FOREIGN PATENT DOCUMENTS

KR 20180125268 A 11/2018

OTHER PUBLICATIONS

Lee, S., Son, K., Lee, J., Jeon, M., Lee, K.B. and Kim, J., 2020. Fabrication of dental crown by optical coherence tomography: a pilot study. IEEE Access, 8, pp. 144969-144975.*
(Continued)

*Primary Examiner* — Zhitong Chen
(74) *Attorney, Agent, or Firm* — United One Law Group LLC; Kongsik Kim; Jhongwoo Peck

(57) ABSTRACT

The present inventive concept relates to a method for obtaining a subgingival marginal shape for a prosthesis design non-invasively by means of an optical coherence tomography (OCT) scanner for obtaining a subgingival marginal shape and an intraoral scanner for obtaining a tooth surface shape, the method including the steps of: obtaining a surface shape of a prepared tooth by means of the intraoral scanner; obtaining the subgingival marginal shape (crown margin line) of the prepared tooth by means of the OCT scanner; and merging the surface shape of the prepared tooth with the subgingival marginal shape to obtain a final three-dimensional shape of the prepared tooth.

1 Claim, 2 Drawing Sheets

(52) U.S. Cl.
CPC .... *G06T 19/20* (2013.01); *G06T 2207/30036* (2013.01); *G06T 2219/2004* (2013.01)

(58) Field of Classification Search
CPC ........ G16H 30/40; G16H 50/50; G16H 20/30; G16H 30/00
See application file for complete search history.

(56) References Cited

OTHER PUBLICATIONS

European Extended Search Report for Application No. 22157848.7, mailed Jul. 8, 2022.
Lee, Sangbong et al., "Fabrication of Dental Crown by Optical Coherence Tomography: A Pilot Study", IEEE Access, IEEE, USA, vol. 8, Aug. 4, 2020, 144969-144975.
Office Action for KR Application 10-2021-0022390 mailed Jun. 8, 2022.

\* cited by examiner

METHOD FOR OBTAINING SUBGINGIVAL MARGINAL SHAPE FOR PROSTHESIS DESIGN NON-INVASIVELY

CROSS REFERENCE TO RELATED APPLICATION

The present application claims the benefit of Korean Patent Application No. 10-2021-0022390 filed in the Korean Intellectual Property Office on Feb. 19, 2021, the entire contents of which are incorporated herein by reference.

BACKGROUND

1. Technical Field

The present disclosure relates to a method for obtaining a subgingival marginal shape for a prosthesis design non-invasively, and more specifically, a method for obtaining a subgingival marginal shape for a prosthesis design non-invasively that is capable of obtaining a shape of a prepared tooth for the prosthesis design using a subgingival marginal shape obtained by means of an optical coherence tomography (OCT) scanner and a shape of a prepared tooth surface obtained by means of an intraoral scanner in a process of a prosthetic treatment.

2. Description of the Related Art

A dental prosthesis is a dental appliance that replaces a missing tooth or covers up tooth defects such as oral function decreasing by a missing tooth and abnormality in shape to thus restore the original function of the tooth.

For example, if a tooth is decayed, a gum disease occurs, or a tooth is lost or broken due to an injury or accident, a prosthetic treatment is performed to restore the tooth having a problem with an original tooth shape.

The dental prosthesis is largely classified into a fixed prosthesis and a removable prosthesis. The fixed prosthesis is needed when a tooth is decayed or broken, without being lost, and thus requires reinforcement or when a tooth is lost to fix an artificial tooth to a position of the lost tooth. Contrarily, the removable prosthesis is detachably fixed, like a denture.

The fixed prosthesis includes a crown put on a tooth, a bridge connecting artificial teeth, and a resin, an inlay, or an onlay that is filled in a cut damaged portion of a tooth.

In the process of the prosthetic treatment, tooth preparation is needed for mounting the crown or bridge. The tooth preparation allows the prosthesis to be mountable and has an influence on a coupling force between the tooth and the prosthesis. The tooth preparation is an important process of cutting the tooth so that the prosthesis cannot be lost or broken.

A conventional intraoral scanner obtains a shape of a prepared tooth only from a surface shape of the prepared tooth. Accordingly, the intraoral scanner is hidden by the gingiva to thus obtain no subgingival marginal shape accurately.

SUMMARY

Accordingly, the present disclosure has been made in view of the above-mentioned problems occurring in the related art, and it is an object of the present inventive concept to provide a method for obtaining a subgingival marginal shape for a prosthesis design non-invasively.

It is another object of the present inventive concept to provide a method for obtaining a subgingival marginal shape for a prosthesis design non-invasively that is capable of obtaining a surface shape of a prepared tooth by means of an intraoral scanner and a subgingival marginal shape of the prepared tooth by means of an OCT scanner so that the prepared tooth surface shape is merged with the subgingival marginal shape to thus acquire the entire shape of the prepared tooth.

To accomplish the above-mentioned objects, according to the present inventive concept, there is provided a method for obtaining a subgingival marginal shape for a prosthesis design non-invasively by means of an optical coherence tomography (OCT) scanner for obtaining a subgingival marginal shape and an intraoral scanner for obtaining a tooth surface shape, the method including the steps of: obtaining a surface shape of a prepared tooth by means of the intraoral scanner; obtaining the subgingival marginal shape (crown margin line) of the prepared tooth by means of the OCT scanner; and merging the surface shape of the prepared tooth with the subgingival marginal shape to obtain a final three-dimensional shape of the prepared tooth.

According to the present inventive concept, desirably, the OCT scanner may be an OCT system.

According to the present inventive concept, desirably, the step of obtaining the subgingival marginal shape (crown margin line) of the prepared tooth may include the step of marking margin lines on the slice images of the OCT scanner that are repeatedly retrieved from the first slice position of a prepared tooth area to the last slice position thereof.

According to the present inventive concept, desirably, the method may further include the step of connecting the marked margin line to the crown margin line.

According to the present inventive concept, desirably, the method may further include the step of transforming the margin line and the crown margin line into STL/PLY formats.

BRIEF DESCRIPTION OF THE DRAWINGS

The above and other objects, features and advantages of the present inventive concept will be apparent from the following detailed description of the preferred embodiments of the invention in conjunction with the accompanying drawings, in which.

DETAILED DESCRIPTION OF THE PREFERRED EMBODIMENTS

Figure 1:
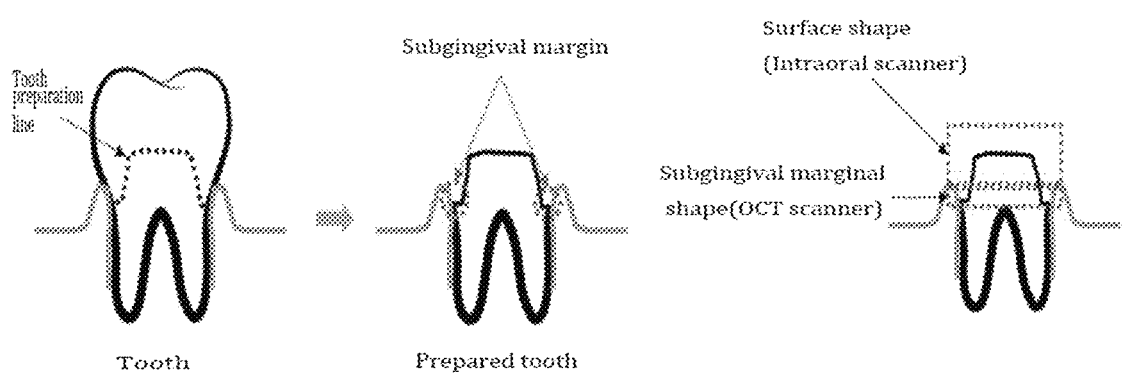
FIG. 1 is a concept view showing a method for obtaining a subgingival marginal shape for a prosthesis design non-invasively according to the present inventive concept.

Objects, characteristics and advantages of the present inventive concept will be more clearly understood from the detailed description as will be described below and the attached drawings. Before the present inventive concept is disclosed and described, it is to be understood that the disclosed embodiments are merely exemplary of the invention, which can be embodied in various forms. An embodiment of the present inventive concept as will be discussed later will be in detail described so that it may be carried out easily by those having ordinary skill in the art, and therefore, this does not limit the idea and technical scope of the invention.

In the description, the thicknesses of the lines or the sizes of the components shown in the drawing may be magnified for the clarity and convenience of the description. In the description, further, the corresponding parts in the embodiments of the present inventive concept are indicated by corresponding reference numerals.

A term 'and/or' includes a combination of a plurality of relevant and described items or any one of a plurality of related and described items. An expression referencing a singular value additionally refers to a corresponding expression of the plural number, unless explicitly limited otherwise by the context. In this application, terms, such as "comprise", "include", or 'have", are intended to designate those characteristics, numbers, steps, operations, elements, or parts which are described in the specification, or any combination of them that exist.

Hereinafter, the present inventive concept will be explained in detail with reference to the attached drawings.

FIG. 1 is a concept view showing a method for obtaining a subgingival marginal shape for a prosthesis design non-invasively according to the present inventive concept.

Referring to FIG. 1, a method for obtaining a subgingival marginal shape for a prosthesis design non-invasively according to the present inventive concept is performed using both of an intraoral scanner for obtaining a tooth surface shape and an OCT scanner for obtaining a subgingival marginal shape.

In specific, the intraoral scanner serves to capture a tooth surface shape. The intraoral scanner projects a light source of a projector onto a tooth surface and produces an image of the tooth surface by a camera to obtain the tooth surface shape.

The subgingival margin is a boundary line of a tooth under the gingiva (the gum) at the time when the tooth is prepared, and the intraoral scanner for obtaining the tooth surface shape is hidden by the gingiva to thus obtain no subgingival marginal shape. However, the OCT scanner obtains the subgingival marginal shape through a tomography technology.

Accordingly, the OCT scanner can obtain the subgingival marginal shape.

Therefore, the tooth surface shape obtained by the intraoral scanner is merged with the subgingival marginal shape obtained by the OCT scanner to thus acquire a final shape of the prepared tooth for a prosthesis design upon a prosthesis treatment.

Figure 2:
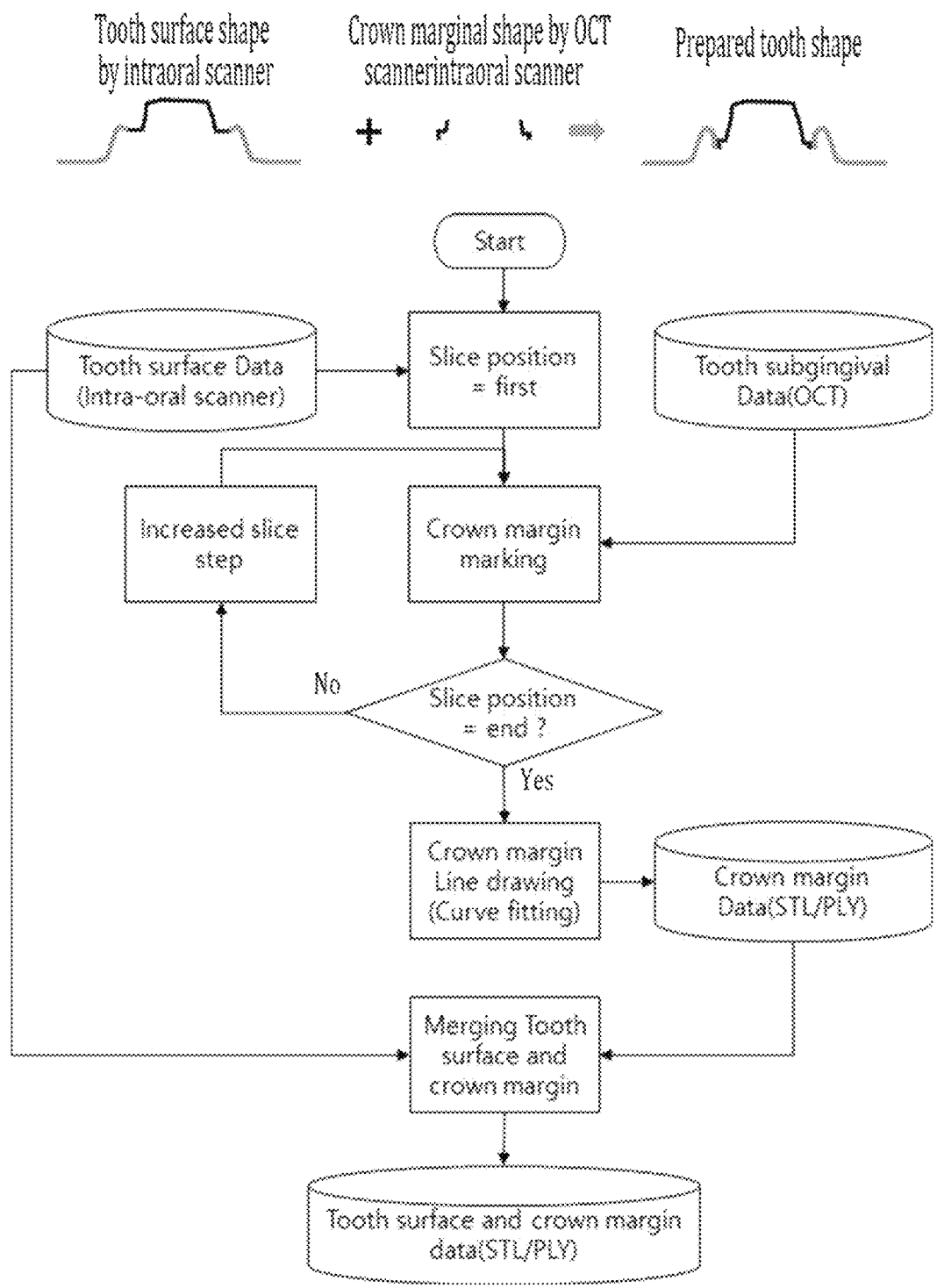
FIG. 2 is a flowchart showing a process of obtaining a final shape of a prepared tooth by merging a prepared tooth surface shape and a crown marginal shape according to the present inventive concept.

FIG. 2 is a flowchart showing a process of obtaining a final shape of a prepared tooth by merging a tooth surface shape and a crown marginal shape according to the present inventive concept.

Referring to FIGS. 1 and 2, the tooth surface shape is obtained by the intraoral scanner, and a slice image of the OCT scanner at a first slice position corresponding to a tooth preparation area on the obtained tooth surface shape is retrieved. Next, a margin portion on the slice image is marked. In this case, the margin portion is a boundary surface of a prepared tooth line.

After that, the slice images of the OCT scanner up to the last slice position of the tooth preparation area are repeatedly retrieved, and a crown margin line on the slice images of the OCT scanner is marked. In this case, the crown margin line is the subgingival margin.

Next, the marked portion is connected to the crown margin line. That is, the boundary surface of the prepared tooth line is connected to the subgingival margin.

The margin portion (boundary surface of the prepared tooth line) and the crown margin line (the subgingival margin) are transformed into data (for example, STL/PLY formats) available in a 3D tool S/W including a CAD.

Lastly, the tooth surface shape data of the intraoral scanner and the crown margin data of the OCT scanner, as the transformed data, are merged with each other, thereby measuring the entire shape of the prepared tooth.

Therefore, the tooth surface shape obtained by the intraoral scanner is merged with the subgingival marginal shape obtained by the OCT scanner to thus acquire a final shape of the prepared tooth for a prosthesis design upon a prosthesis treatment.

As set forth in the foregoing, the present inventive concept can obtain the subgingival marginal shape by means of the OCT scanner to acquire the entire shape of the prepared tooth for a good quality of prosthesis design.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above teachings. It is therefore intended that the scope of the invention be limited not by this detailed description, but rather by the claims appended hereto.

What is claimed is:

1. A method for obtaining a subgingival marginal shape for a prosthesis design non-invasively by means of an optical coherence tomography (OCT) scanner for obtaining a subgingival marginal shape and an intraoral scanner for obtaining a tooth surface shape, the method comprising the steps of:

obtaining a surface shape of a prepared tooth by means of the intraoral scanner;

obtaining the subgingival marginal shape (crown margin line) of the prepared tooth by means of the OCT scanner; and merging the surface shape of the prepared tooth with the subgingival marginal shape to obtain a final three-dimensional shape of the prepared tooth, wherein the step of obtaining the subgingival marginal shape (crown margin line) of the prepared tooth comprises the steps of:

marking margin portions on the slice images of the OCT scanner that are repeatedly retrieved from the first slice position of a prepared tooth area to the last slice position thereof; and connecting the marked margin portions to form the crown margin line.

* * * * *